United States Patent [19]

Wade

[11] Patent Number: 5,716,334
[45] Date of Patent: Feb. 10, 1998

[54] BODY PART IMMOBILIZER

[76] Inventor: Larry E. Wade, 2240 Edgewood Dr., Panama City, Fla. 32405

[21] Appl. No.: 516,992

[22] Filed: Aug. 18, 1995

[51] Int. Cl.$^6$ .................................................. A61F 5/00
[52] U.S. Cl. .................. 602/6; 602/15; 602/14; 128/882; 5/651
[58] Field of Search .................. 602/5–8, 12, 14, 602/15, 23; 128/845–847, 877–878, 882; 5/624, 648, 650, 651

[56] References Cited

U.S. PATENT DOCUMENTS

| | | | |
|---|---|---|---|
| 2,478,497 | 8/1949 | Morrison | 5/651 X |
| 3,511,233 | 5/1970 | Holy, Jr. | 602/65 X |
| 3,931,654 | 1/1976 | Spann | 5/650 |
| 3,946,451 | 3/1976 | Spann | 5/650 |
| 4,071,031 | 1/1978 | Lowman | 5/648 X |
| 4,082,257 | 4/1978 | Strickland | 5/606 X |
| 4,265,232 | 5/1981 | Stonich | 128/845 |
| 4,383,526 | 5/1983 | Robins | 602/15 |
| 5,046,487 | 9/1991 | Scott | 5/650 X |
| 5,289,828 | 3/1994 | Toth | 128/845 |
| 5,477,866 | 12/1995 | Davenport | 128/845 |

*Primary Examiner*—Linda C. Dvorak
*Attorney, Agent, or Firm*—Peter Loffler

[57] ABSTRACT

A body part immobilizer is disclosed. The device comprises an arm, leg, or head cast, each having a cavity means for receiving the respective body part therein. Securement straps are provided for securely holding the body part in the appropriate cast member while tie-down straps can be used to secure the device to a table, bed, etc. Drains means are located within each cast member for draining fluid therefrom.

7 Claims, 5 Drawing Sheets

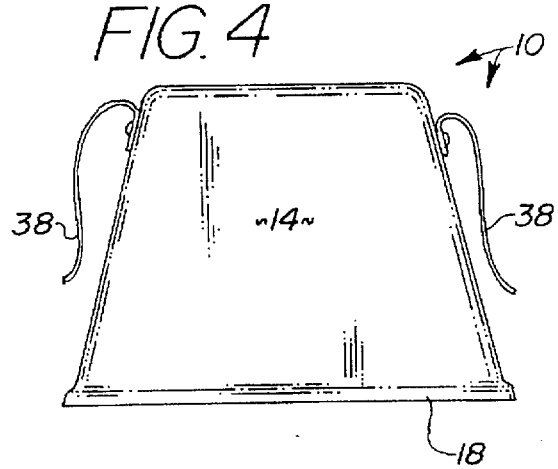
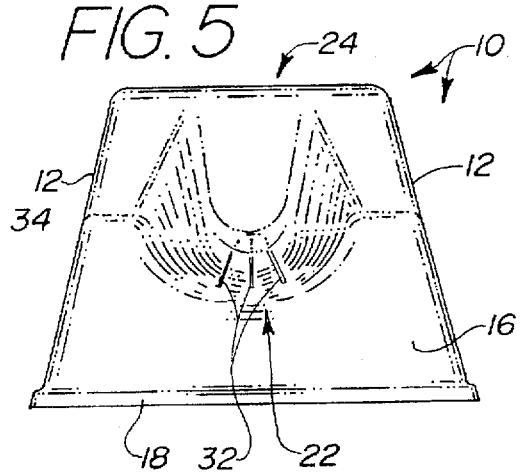
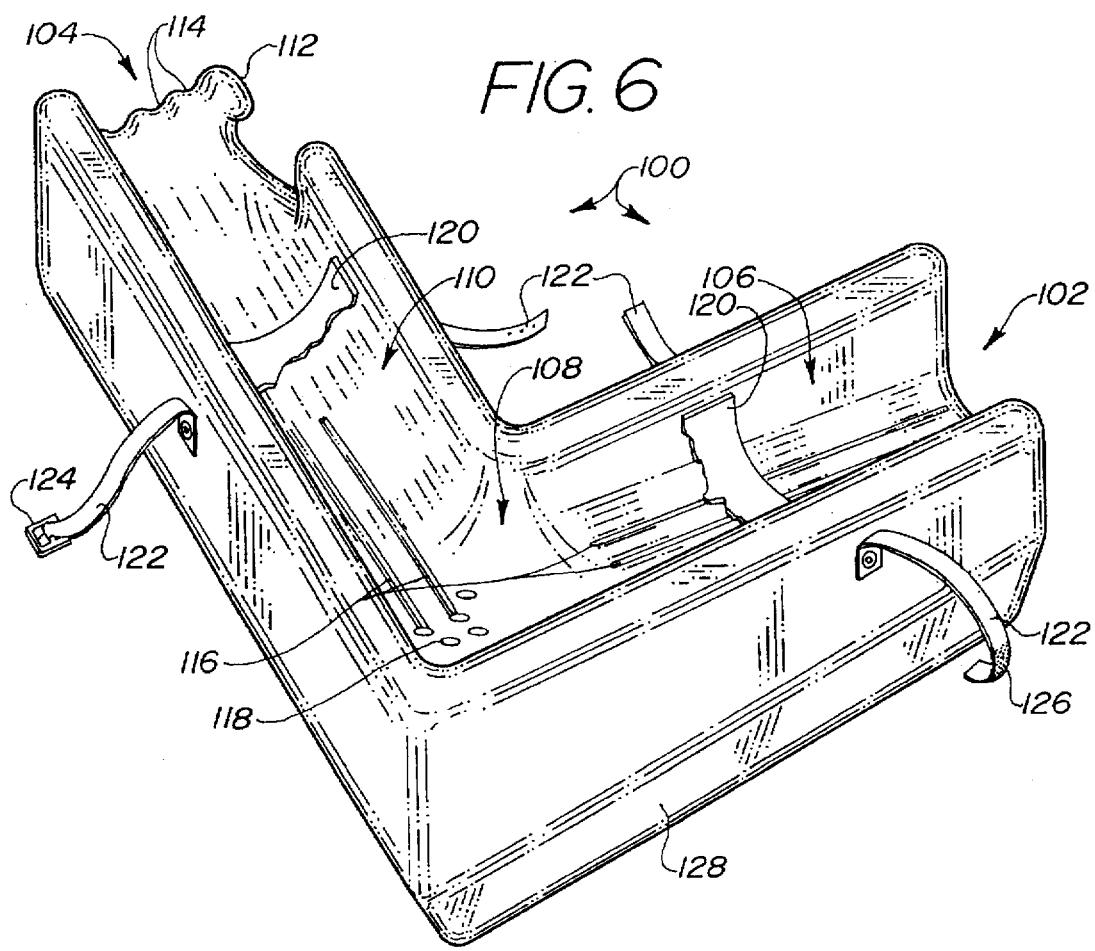

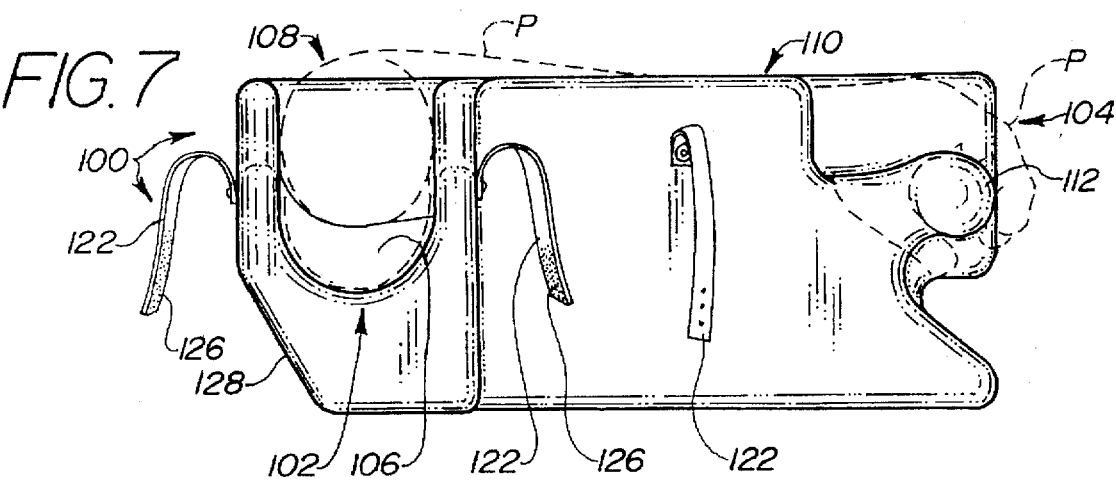
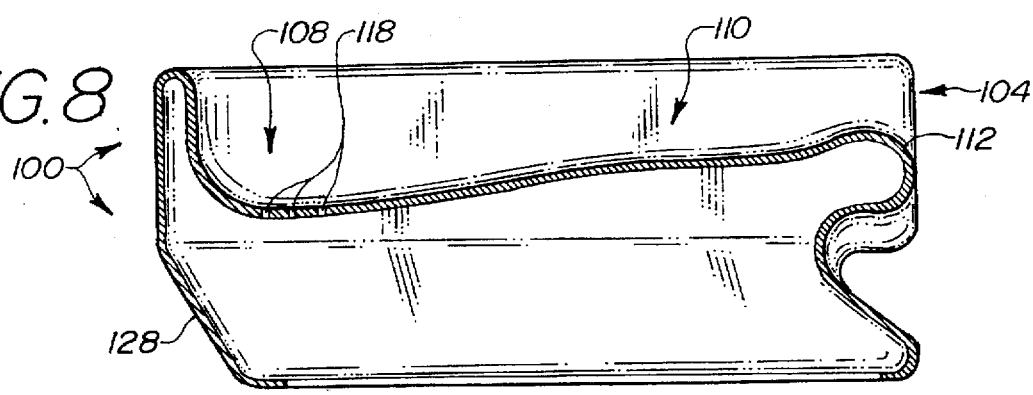
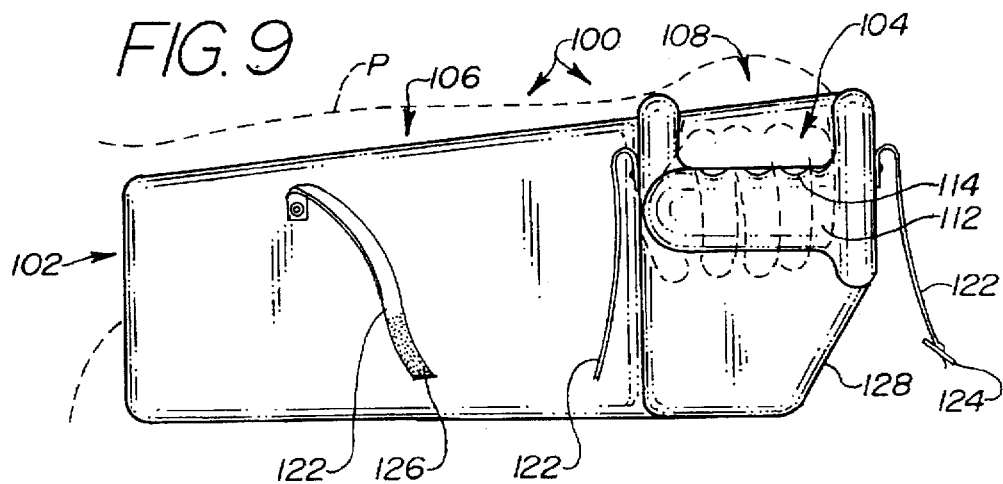

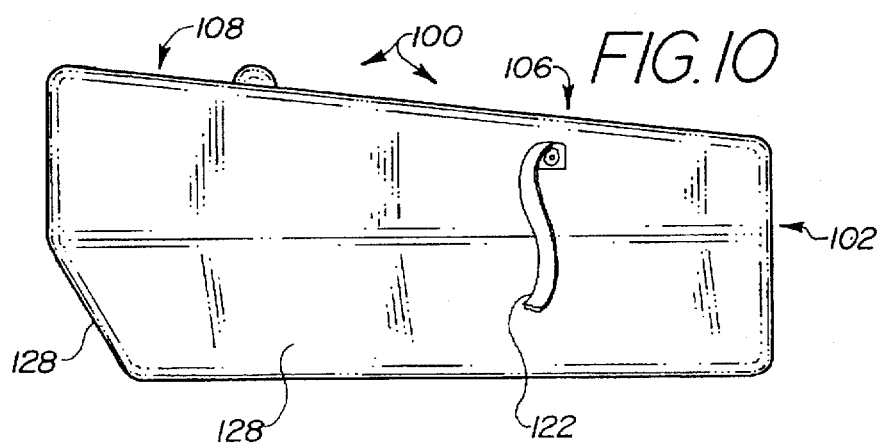
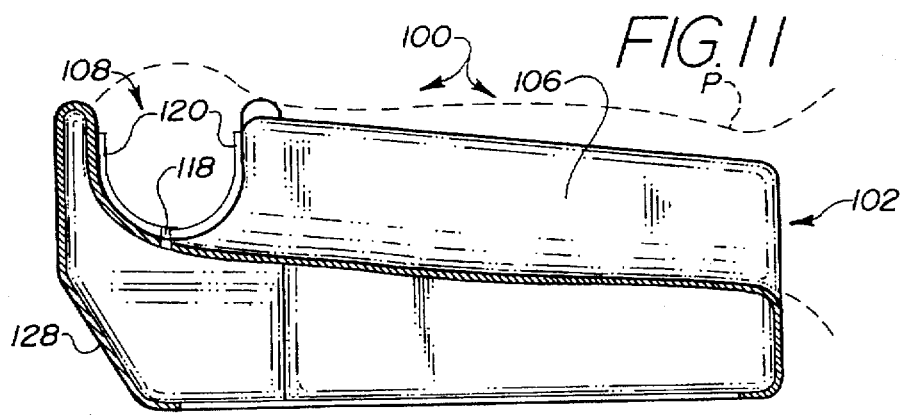
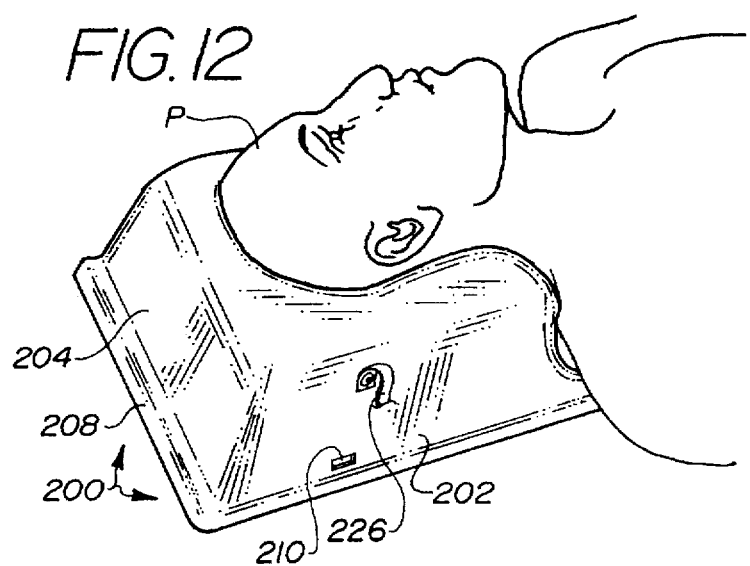

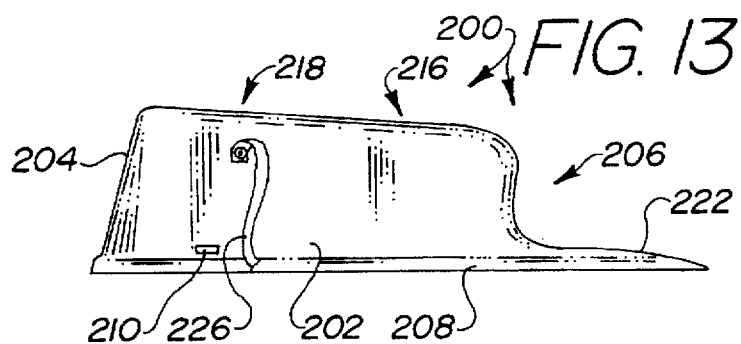
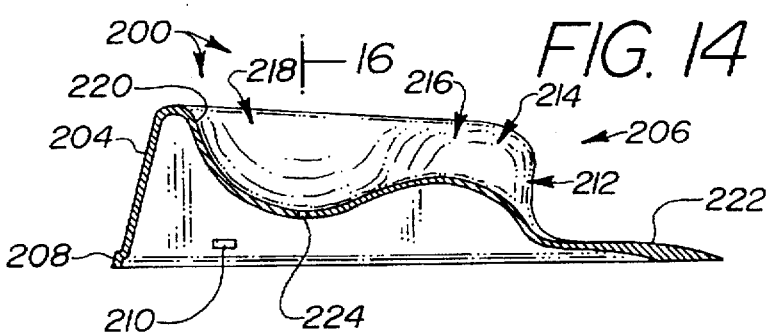
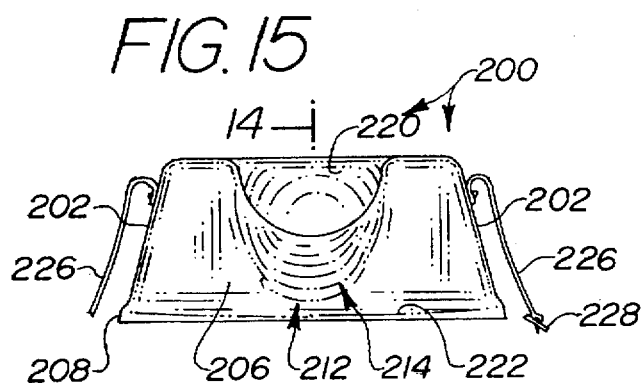
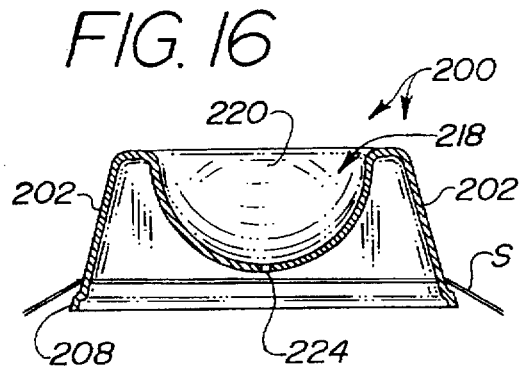

BODY PART IMMOBILIZER

BACKGROUND OF THE INVENTION

1. Field of the Invention

The present invention relates to a body part immobilizer that holds various parts of the body in a stable and secure manner

2. Background of the Prior Art

After a body part, such as a leg, an arm, or the head, has been injured, the body part may require immobilization. Such is also the case when the body part is recuperating from surgery or during surgery on the body part. Several techniques exist to accomplish the immobilization task including many tie-down methods. Although such techniques may accomplish the intended goal, they tend to suffer from one or more drawbacks.

Many immobilization techniques require the use of elaborate devices such as cables and pulleys. Such devices are expensive and are difficult to use and may interfere with access to the body part during a medical procedure and post-operative care. Bathing or otherwise washing down of the immobilized body part may prove impossible. Tie-down methods are uncomfortable and typically require device deactivation when the user is to be transported.

A device is needed that immobilizes a person's arm, leg or head without the need for elaborate equipment. Such a device should be simple and straightforward to use and should be comfortable for the user. Access to the immobilized body part should not be unduly restricted by the use of such a device.

SUMMARY OF THE INVENTION

The body part immobilizer of the present invention meets the above-stated needs in the art. The device can securely hold a user's arm, leg, or head.

An arm is received within an arm cast having a generally L-shaped configuration. A generally U-shaped cavity defines the upper arm reception area while a second generally U-shaped cavity, integrally joining the first cavity, defines the lower arm reception area. A hand grip is located at the end of the second cavity.

A leg is received within a leg cast having a generally rectangular-shaped configuration. A generally U-shaped cavity defines the leg reception area while a well, located at the end of the cavity, defines an ankle reception area and foot base.

A head is received within a head cast having a generally rectangular-shaped configuration. A generally U-shaped cavity, defining a neck reception area, terminates in a well defining a head reception area. A shoulder reception flange is also provided.

Each body part receiving cavity of the arm cast, leg cast, and head cast is padded for increased user comfort. Each cast member has drain means located therein for draining fluid from the cavity areas. Securement straps hold the appropriate body part in place within the respective cast member while tie-down straps can be used to secure the cast member to a table, bed or other similar surface.

The device of the present invention is simple to make and use. It does not require the manipulation of elaborate equipment. Once a body part is secured within a cast member, the user and secured body part can be transported without difficulty. A secured body part is easily accessible for medical and hygienic procedures that need to be performed upon the immobilized body part. The drain means assure that the body part may be washed down during utilization of the device.

BRIEF DESCRIPTION OF THE DRAWINGS

FIG. 4 is a left elevation view of the leg cast embodiment of the present invention.

FIG. 5 is a left section view of the leg cast embodiment of the present invention.

FIG. 6 is a perspective view of the arm cast embodiment of the present invention.

FIG. 7 is a front elevation view of the arm cast embodiment of the present invention.

FIG. 8 is a rear elevation view of the arm cast embodiment of the present invention.

FIG. 9 is a rear section view of the arm cast embodiment of the present invention.

FIG. 10 is a left elevation view of the arm cast embodiment of the present invention.

FIG. 11 is a left section view of the arm cast embodiment of the present invention.

FIG. 12 is a perspective view of the head cast embodiment of the present invention.

FIG. 13 is a front elevation view of the head cast embodiment of the present invention.

FIG. 14 is a front section view of the head cast embodiment of the present invention.

FIG. 15 is a left elevation view of the head cast embodiment of the present invention.

FIG. 16 is a left section view of the head cast embodiment of the present invention.

Similar reference numerals refer to similar parts throughout the several views of the drawings.

DETAILED DESCRIPTION OF THE PREFERRED EMBODIMENT

Figure 1:
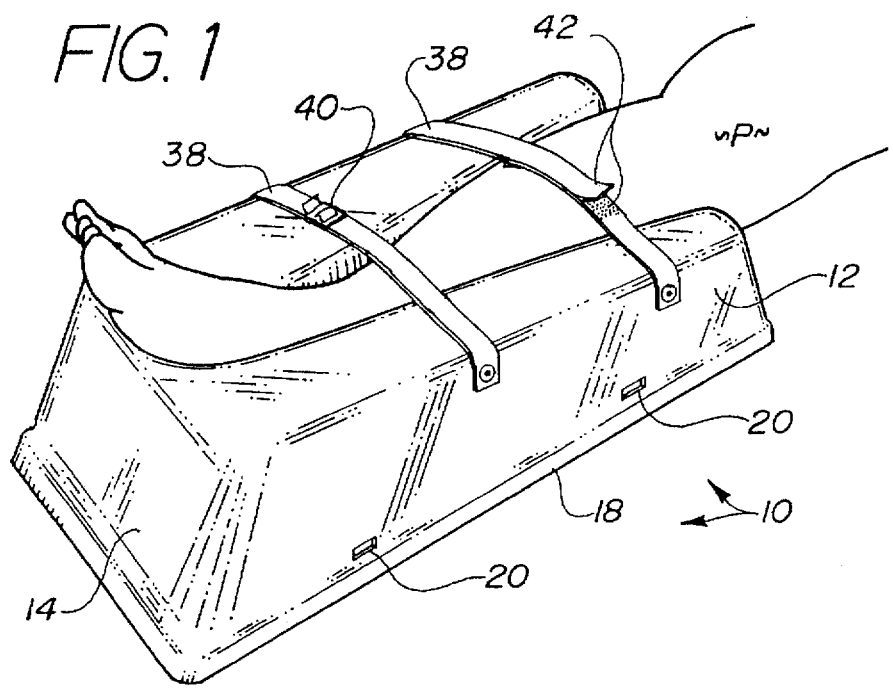
FIG. 1 is a perspective view of the leg cast embodiment of the present invention.
Figure 2:
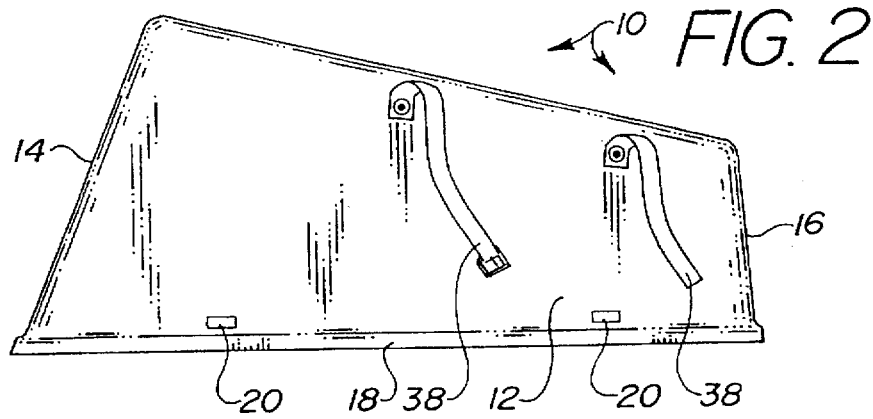
FIG. 2 is a front elevation view of the leg cast embodiment of the present invention.
Figure 3:
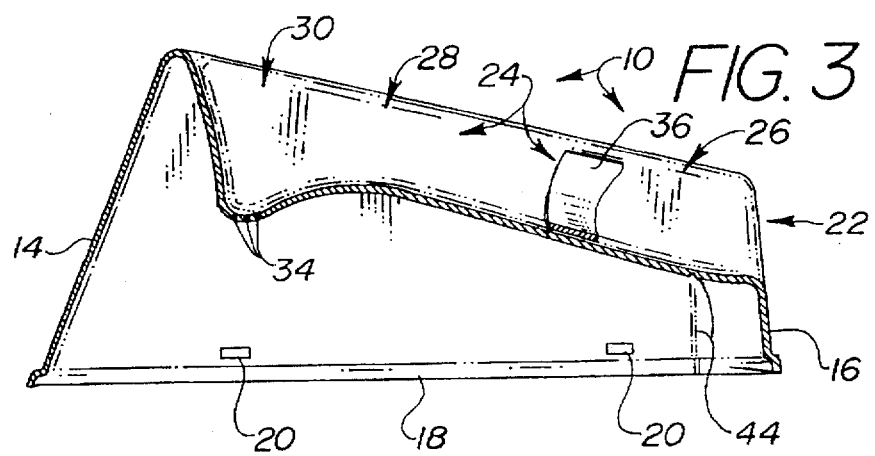
FIG. 3 is a rear elevation view of the leg cast embodiment of the present invention.

The body part immobilizer of the present invention comprises a generally rectangular-shaped leg cast unit 10. The leg cast unit 10 has a pair of side walls 12 disposed in parallel relation, a back wall 14 integrally joining the pair of side walls 12, and a front 16 opposing the back wall 14. A flange 18 encompasses the base of the leg cast 10. A plurality of slotted portions 20 are optionally distributed at several locations near the flange 18. The slotted portions 20 receive tie-down straps. When rested flat upon a surface, the unit 10 has an upward slope from front to back. The front 16 of the device has an opening 22. Extending inwardly from the opening 22 is a generally U-shaped cavity 24. As seen in FIG. 5, proceeding from the opening 22, the cavity 24 slopes upwardly defining a leg well 26, then downwardly defining an ankle well 28, then upwardly defining a foot base 30. A user places his ankle into the ankle well 28 such that the bottom of the user's foot rests against the foot base 30 and the user's calf is received within the leg well 26.

The leg well 26 has a series of groove troughs 32, located therein, for draining fluid from the leg well 26 out through the opening 22. An aperture 34, located at the bottom of the ankle well 28, drains fluid from the ankle well 28. The groove troughs 32 and the aperture 34 permit the user's leg to be washed down while securely held within the unit 10.

The leg well 26, the ankle well 28, and the foot base 30, can each be padded 36 for increased user comfort.

One or more securement straps 38 extend from one of the side walls 12 to the opposing side wall 12 in order to help secure a user's leg within the unit 10. Each securement strap 38, after being draped over the user's leg, can be securely held in place by a buckle 40, cooperating hook and loop material VELCRO™, or other similar means. If necessary, the device can be secured to a table, bed, or similar location, by passing one or more tie-down straps through the slotted portions 18. A perforation 44 extends from the first side wall 12 to the opposing side wall 12 so that an end portion of the leg cast unit 10 can be broken off at the perforation 44 for sizing of the device for a particular user.

As seen in FIGS. 6–11, an alternate embodiment of the device comprises a generally L-shaped arm cast unit 100. The arm cast 100 has a first opening 102 and a second opening 104. A generally U-shaped first cavity 106 extends from the first opening to a bend point 108. A generally U-shaped second cavity 110 extends from the second opening 104 and integrally meets the first cavity 106 resulting in a continuous cavity extending from the first opening 102 to the second opening 104. The first cavity's meeting of the second cavity 110 can be perpendicular, at an acute angle, or at an obtuse angle. The continuous cavity receives an arm of a user with the upper arm received in the first cavity 104, the elbow received at the bend point 108, and the lower arm received in the second cavity 110.

As seen, the first cavity 106 has an upward slope from the first opening 102 to the bend point 108 while the second cavity 110 has an upward slope from the bend point 108 to the second opening 106.

A hand grip 112 is located at the second opening 104. Once a user's arm is positioned within the unit 100, the user's hand grasps the hand grip 112. A plurality of finger wells 114 increase gripability of the hand grip 112.

The first cavity 106 and the second cavity 110 each have a series of groove troughs 116, located therein, for draining fluid therefrom. An aperture 118 is locatable at the bend point 108 in order to prevent fluid accumulation therein.

The first cavity 106 and the second cavity 110 can each be padded 120 for increased user comfort.

One or more securement straps 122 extend from one of the side walls of the arm cast 100 to the opposing side wall of the arm cast 100 in order to help secure a user's arm within the device. Each securement strap 122, once draped over the user's arm, can be securely held in place by a buckle 124, cooperating hook and loop material VELCRO™ 126, or other similar means.

As seen, the sidewalls of the arm cast unit 100 have beveled sidewalls 128. The beveled sidewalls 128 permit the device to be secured to a surface of choice at various angles of inclination.

As seen in FIGS. 12–16 a second alternate embodiment of the present invention comprises a generally rectangular-shaped head cast unit 200 having a pair of side walls 202 disposed in parallel relation, a back wall 204 integrally joining the pair of side walls 202, and a front 206 opposing the back wall 204. A flange 208, extending outwardly, encompasses the base of the head cast 200. A plurality of slotted portions 210 are optionally distributed at several locations near the flange 208. The slotted portions 210 receive tie-down straps. When rested flat upon a surface, the unit 200 has an upward slope from front to back. The front 206 of the device has an opening 212. Extending inwardly from the opening 212 is a generally U-shaped cavity 214. As seen in FIG. 16, proceeding from the opening 212, the cavity 214 slopes first upwardly defining a neck well 216, then downwardly defining a head well 218, then upwardly defining a head base 220. A user places his head into the head well 218 such that the top of his head rests against the head base 220 and the user's neck rests within the neck well 216.

An aperture 224, located at the bottom of the head well 218, drains fluid from the head well 218. The aperture 224 permits the user's head to be washed down while securely held within the unit 200.

The neck well 216, the head well 218, and the head base 220, can each be padded 224 for increased user comfort.

One or more securement straps 226 extend from one of the side walls 202 to the opposing side wall 202 in order to help secure a user's head within the device. Each securement strap 226, once draped over the head, can be held in place by a buckle 228, cooperating hook and loop material VELCRO™ 230, or other similar means. If necessary, the device can be secured to a table, bed, or similar location, by passing one or more tie-down straps through the slotted portions 208.

A shoulder flange 222 extends outwardly from the front 206 receives the shoulders of a user. The shoulder flange 222 may also be padded 224.

While the invention has been particularly shown and described with reference to embodiments thereof, it will be recognized by those skilled in the art that various changes in form and detail may be made without departing from the spirit and scope of the invention.

I claim:

1. A leg immobilizing device for securely holding a person's leg, ankle and foot comprising:

a unitary cast, having a generally rectangular-shaped base, a generally vertically oriented first side, a generally vertically oriented second side opposite the first side, a generally vertically oriented front, a back opposing the front, and a top that is tapered relative to the base;

an arcuate cavity disposed within the top and having a first portion, a second portion, and a third portion, the first portion extending inwardly from the front and sloping upwardly relative to the base, the second portion extending from the first portion and sloping downwardly relative to the base, and the third portion extending from the second portion and sloping upwardly relative to the base and terminating at the top; and wherein the first portion is adapted to receive the leg, the second portion is adapted to receive the ankle, and the third portion is adapted to receive the foot.

2. The device as in claim 1 further comprising:

a) a plurality of groove troughs, located within the first portion, for draining fluid from the cavity; and b) at least one aperture, located within the second portion, for draining fluid from the second portion.

3. The device as in claim 1 further comprising:
a) at least one securement strap, attached to the first side;
b) at least one securement means, in corresponding number to the number of securement straps, located on the second side; and
wherein when the user's leg is received within the device, the securement straps are draped over the leg and are securely held by the securement means.

4. The device as in claim 3 wherein the securement means comprises a buckle or cooperating hook and loop material.

5. The device as in claim 1 to further include a perforation, located proximately to the front and extending from the first side to the second side, for optionally decreasing the length of the device.

6. The device as in claim 1 further comprising a plurality of spaced apart slotted portions, located proximately to the base of the leg cast, for receiving tie-down straps.

7. The device as in claim 1 further comprising a padded layer covering the first portion, the second portion, and the third portion.

* * * * *